(12) United States Patent
Wang et al.

(10) Patent No.: US 12,208,365 B2
(45) Date of Patent: Jan. 28, 2025

(54) GENE CHIP AND METHOD OF PREPARING THE SAME

(71) Applicant: BGI SHENZHEN, Shenzhen (CN)

(72) Inventors: Zhao-Hui Wang, Shenzhen (CN); Hui Wang, Shenzhen (CN); Cheng-Mei Xing, Shenzhen (CN); Han-Dong Li, Shenzhen (CN); Wen-Wei Zhang, Shenzhen (CN); Jay Willis Shafto, Shenzhen (CN); Mei-Hua Gong, Shenzhen (CN); Jin Yang, Shenzhen (CN); Yin-Ling Luo, Shenzhen (CN); Zhen-Hua Zhang, Shenzhen (CN); Yuan Li, Shenzhen (CN); Xue-Qin Jiang, Shenzhen (CN)

(73) Assignee: BGI SHENZHEN, Shenzhen (CN)

( * ) Notice: Subject to any disclaimer, the term of this patent is extended or adjusted under 35 U.S.C. 154(b) by 1027 days.

(21) Appl. No.: 17/266,994

(22) PCT Filed: Aug. 15, 2018

(86) PCT No.: PCT/CN2018/100692
§ 371 (c)(1),
(2) Date: Feb. 8, 2021

(87) PCT Pub. No.: WO2020/034122
PCT Pub. Date: Feb. 20, 2020

(65) Prior Publication Data
US 2021/0162365 A1    Jun. 3, 2021

(51) Int. Cl.
*B01J 19/00* (2006.01)
*C40B 40/06* (2006.01)

(52) U.S. Cl.
CPC .. *B01J 19/0046* (2013.01); *B01J 2219/00529* (2013.01); *B01J 2219/00722* (2013.01); *C40B 40/06* (2013.01)

(58) Field of Classification Search
None
See application file for complete search history.

(56) References Cited

FOREIGN PATENT DOCUMENTS

| JP | 2001272402 A | 10/2001 | |
|---|---|---|---|
| WO | WO-2013066975 A1 * | 5/2013 | .......... B01J 19/0046 |

OTHER PUBLICATIONS

Radoje Drmanac et al., Human Genome Sequencing Using Unchained Base Reads on Self-Assembling DNA Nanoarrays, Science, Jan. 1, 2010, pp. 78-81, vol. 327, No. 5691.

* cited by examiner

*Primary Examiner* — Kaijiang Zhang
(74) *Attorney, Agent, or Firm* — ScienBiziP, P.C.

(57) ABSTRACT

A gene chip includes a chip carrier, a plurality of DNA nanoballs assembled on the chip carrier, and a polymer film formed on the chip carrier and wrapping the DNA nanoballs. The polymer film includes at least one of a film of a positively charged polymer, a film of a positively charged polymer which is modified, a film of a zwitterionic polymer, and a composite polymer film. The composite polymer film is formed by a layer-by-layer self-assembly process of a positively charged polymer and a negatively charged polymer. The gene chip has good sequencing quality and different functions can be achieved by coating with different polymers, such as the chip surface rapidly drying out and surface non-specific adsorption. A method of preparing a gene chip is further disclosed.

19 Claims, 3 Drawing Sheets

GENE CHIP AND METHOD OF PREPARING THE SAME

FIELD

The subject matter relates to biotechnology, and more particularly, to a gene chip and a method of preparing the gene chip.

BACKGROUND

A gene chip is a DNA chip, which is a carrier for gene sequencing. By fixing a specific single stranded DNA library to a surface of the carrier, the gene chip is subjected to a series of biochemical reactions to read the sequence of the specific single stranded DNA library, thereby achieving the purpose of gene sequencing.

A gene sequencing instrument can use a gene chip including an array of DNA nanoballs (DNB). In this gene chip, the DNA nanoballs need to be stably present on the surface and not be damaged or washed away by sequencing reagents.

A commonly used production method of a gene chip includes aminating a surface of a silicon wafer and fixing the DNA nanoballs to the surface of the silicon wafer by electrostatic and hydrophobic interactions between the DNA nanoballs, phi29 DNA polymerases, and amino groups. However, the DNA nanoballs fixed by above method is not stable, and part of the DNA nanoballs can be washed away by the sequencing reagents during the sequencing process. One solution is to use a protein film to protect the adsorbed DNA nanoballs. Although the protein film can give protection, a protein is a molecule with a relatively high molecular weight and has hydrophobic cavities, which renders the surface of the protein film nonspecific adsorptive. In addition, since the protein has been denatured, its water retention is greatly reduced, and the chip is likely to dry out too quickly.

SUMMARY

Thus, a gene chip providing a good stability of DNA nanoballs on a surface of a chip carrier and without the problems of nonspecific adsorption and surface dryness, and a method of preparing such gene chip are needed.

The present disclosure provides a gene chip including a chip carrier, a plurality of DNA nanoballs assembled on the chip carrier, and a polymer film formed on the chip carrier and wrapping the DNA nanoballs. The polymer film includes at least one of a film of a positively charged polymer, a film of a positively charged polymer which is modified, a film of a zwitterionic polymer, and a composite polymer film. The composite polymer film is formed by a layer-by-layer self-assembly of the positively charged polymer and a negatively charged polymer.

Furthermore, the positively charged polymer includes at least one of chitosan, polylysine, polyethyleneimine, poly-N,N-dimethylaminoethyl methacrylate, and polymer with pyridyl side groups, imidazole salt side groups, or quaternary phosphate salt side groups. The zwitterionic polymer includes at least one of polyacrylamide polymer and betaine polymer. The negatively charged polymer includes at least one of sodium hyaluronate, sodium polyacrylate, and sodium polystyrene sulfonate. The positive polymer is modified by polyethylene glycol or polyethylene glycol derivatives.

Furthermore, the chip carrier is an aminated silicon wafer.

The present disclosure further provides a method of preparing of a gene chip, the method includes placing a chip carrier carrying DNA nanoballs into a first reaction solution to react to form a first layer of polymer film covering the DNA nanoballs on the chip carrier. The first reaction solution includes at least one of a positively charged polymer, a positively charged polymer which is modified, and a zwitterionic polymer.

Furthermore, the preparation method further includes placing the chip carrier, after reacting in the first reaction solution, into a second reaction solution to react to form a second layer of polymer film on the first layer of polymer film. The second reaction solution includes a negatively charged polymer.

Furthermore, the preparation method further includes introducing a PBS solution on the chip carrier to remove excess polymers.

Furthermore, after introducing the PBS solution on the chip carrier to remove recess polymers, the preparation method further includes introducing neutral buffer solution.

Furthermore, the positively charged polymer includes at least one of chitosan, polylysine, polyethyleneimine, poly-N,N-dimethylaminoethyl methacrylate, and polymer with pyridyl side groups, imidazole salt side groups, or quaternary phosphate salt side groups. The zwitterionic polymer includes at least one of polyacrylamide polymer and betaine polymer. The negatively charged polymer includes at least one of sodium hyaluronate, sodium polyacrylate, and sodium polystyrene sulfonate. The positive polymer is modified by the application of polyethylene glycol or polyethylene glycol derivatives.

Furthermore, a concentration of polymers of the first reaction solution is about 1 to 2 mg/mL, and a reaction time in the first reaction solution is about 3 minutes. A concentration of polymers of the second reaction solution is about 2 mg/mL, and a reaction time in the second reaction solution is about 3 minutes. A dispersion liquid of the first reaction solution is a neutral buffer solution or a weakly acidic buffer solution with a pH of 5.5 or more, and a dispersion liquid of the second reaction solution is a neutral buffer solution.

Furthermore, the preparation method further includes placing the chip carrier into a buffer solution containing DNA nanoballs, causing the DNA nanoballs to be assembled on the surface of the chip carrier.

Furthermore, after placing the chip carrier into a buffer solution containing DNA nanoballs, alcohol is introduced to dewater the DNA nanoballs.

In the gene chip prepared by the method of the present disclosure, the stability of the DNA nanoballs on the surface of the gene chip is much improved, and is able to meet the sequencing stability (SE100+PE100, 200 cycles in total). The hydrophilic polymer film formed on the surface of the chip carrier promotes water retention, thereby avoiding the problem of surface dryness. When the polymer film contains anti-protein components such as polyethylene glycol, non-specific adsorption characteristics of the gene chip surface are no longer present.

Implementations of the present technology will now be described, by way of example only, with reference to the attached figures.

DETAILED DESCRIPTION

In order to be able to understand the object, features and advantages of the embodiments of the present disclosure, implementations of the disclosure will now be described, by way of embodiments only, with reference to the drawings. It should be noted that non-conflicting details and features in the embodiments of the present disclosure may be combined with each other.

In the following description, specific details are explained in order to make the embodiments of the present disclosure understandable. The described embodiments are only a portion of, rather than all, of the embodiments of the present disclosure of them. Based on the embodiments of the present disclosure, other embodiments obtained by a person of ordinary skill in the art without creative work shall be within the scope of the present disclosure.

The present disclosure provides a gene chip. The gene chip includes a chip carrier, a plurality of DNA nanoballs, and a polymer film. The DNA nanoballs are assembled on the carrier chip. The polymer film is formed on the carrier chip and wraps the DNA nanoballs.

The polymer film includes at least one of a film of a positively charged polymer, a film of a positively charged polymer which is modified, a film of a zwitterionic polymer, and a composite polymer film. The composite polymer film is formed by a layer-on-layer self-assembly process of the positively charged polymer and a negatively charged polymer. The polymer film is hydrophilic.

The positively charged polymer includes, but is not limited to, chitosan, polylysine, polyethyleneimine, poly-N,N-dimethylaminoethyl methacrylate, or a polymer with pyridyl side groups, imidazole salt side groups, or quaternary phosphate salt side groups. The negatively charged polymer includes, but is not limited to, sodium hyaluronate, sodium polyacrylate, or sodium polystyrene sulfonate. The zwitterionic polymer includes, but is not limited to, polyacrylamide polymer or betaine polymer.

The positive charged polymer may be modified by polyethylene glycol (PEG) or polyethylene glycol derivatives.

Figure 1:
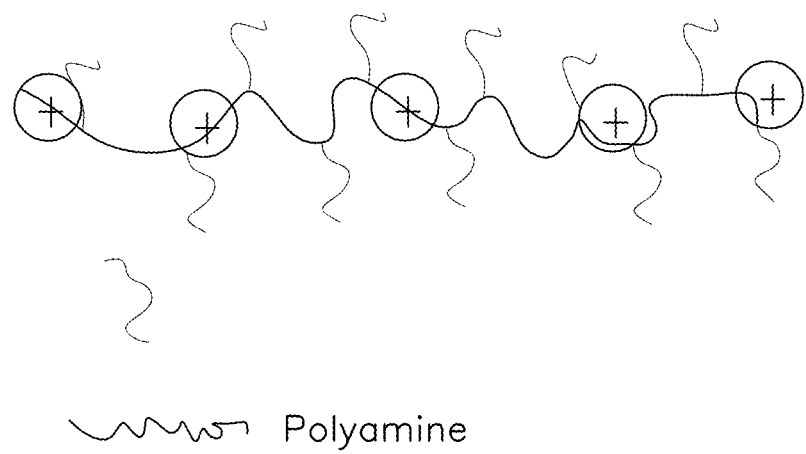
FIG. 1 is a structural diagram of a modified polymer according to the present disclosure.

FIG. 1 is a structural diagram of a modified polymer. In the positively charged polymer which is modified, the main chain is a positively charged polymer, the side chain can be modified with PEG to give anti-protein properties.

The chip carrier is made of glass, metal, silicon wafer, nylon film, plastic, or other materials with chemical surface treatment. The chemical surface treatment is carried out on the surface of the chip carrier such that functional groups with biochemical activities such as aldehyde, carboxyl, epoxy, amino, or the like are formed on the surface of the chip carrier. These functional groups bond the biomolecules, so as to fix the DNA nanoballs. In one embodiment, the chip carrier is an aminated silicon wafer.

The DNA nanoballs are prepared using a kit produced by BGI (The Beijing Genomics Institute). In one embodiment, the DNA nanoballs are prepared by the following steps: 40 fmol of circular ssDNA (single stranded DNA) library is diluted with water to a constant volume of 20 uL, then 20 uL of buffer solution for making the DNB, again produced by BGI, is added. The mixture is mixed thoroughly, heated at 95 degrees Celsius for 1 minute, at 65 degrees Celsius for 1 minute, and at 40 degrees Celsius for 1 minute. The mixture is then cooled to 4 degrees Celsius and 40 uL of polymerase mixture (making DNB Enzyme Mix V2.0) and 4 uL of polymerase mixture II (making DNB Enzyme Mix II V2.0) are added into the cooled solution. After being mixed thoroughly, amplification is performed at 30 degrees Celsius for 20 minutes, and the temperature is cooled to 4 degree Celsius. Finally, 20 uL of stop buffer solution (Stopping DNB RXN Buffer) is added to the cooled solution to stop the amplification. In one embodiment, after stopping the amplification, Qubit ssDNA reagent from Invitrogen is used to test the concentration of the obtained DNB.

In the gene chip of the present disclosure, the DNA nanoballs are stable on the surface of the chip carrier. According to the sequencing quality, the stability of the DNA nanoballs on the surface of the chip carrier meets the sequencing stability (SE100+PE100, 200 cycles in total). The hydrophilic polymer film formed on the surface of the chip carrier makes the surface of the gene chip water-retentive, thereby avoiding the problem of surface dryness. If the surface of the gene chip dries out, the DNA nanoballs on the surface will be destroyed, and destroyed DNA nanoballs cannot obtain the fluorescing information for sequencing, seriously affecting the data throughput of sequencing. When the polymer film includes anti-protein components such as polyethylene glycol, the gene chip has a surface without nonspecific adsorption characteristics.

The present disclosure further provides a preparation method of the above gene chip, the preparation method includes the following steps:

101, a chip carrier is placed in a buffer solution containing DNA nanoballs for reaction to assemble the DNA nanoballs on the surface of the chip carrier. The chip carrier is a an aminated silicon wafer, and the reaction time is 30 minutes.

In one embodiment, step 101 includes adding DNA nanoballs to a DNB loading buffer solution at a ratio of 3:1 to form a mixture, the pH of the mixture being about 4.7; introducing a buffer solution containing the DNA nanoballs to the aminated silicon wafer and standing for 30 minutes.

102, the chip carrier with DNA nanoballs is placed in a first reaction solution for reaction to form a first layer of polymer film covering the DNA nanoballs on the chip carrier. The first reaction solution includes at least one of a positively charged polymer, a positively charged polymer which is modified, and a zwitterionic polymer. The reaction time is 3 minutes. A concentration of polymers of the first reaction solution is about 1 to 2 mg/mL. A dispersion liquid of the first reaction solution is a neutral buffer solution, such as a phosphate buffer saline (PBS) solution, TE buffer solution, or the like, or a weakly acidic buffer solution (pH of 5.5 or more), such as citric acid potassium citrate buffer solution. The above polymers are dispersed in the dispersion liquid to form the first reaction solution.

The positively charged polymer includes, but is not limited to, chitosan, polylysine, polyethyleneimine, poly-N,N-dimethylaminoethyl methacrylate, or a polymer with pyridyl side groups, imidazole salt side groups, or quaternary phosphate salt side groups. The zwitterionic polymer includes, but is not limited to, polyacrylamide polymer or betaine polymer. The modified positive charged polymer may be modified by polyethylene glycol or polyethylene glycol derivatives.

In one embodiment, step 102 includes introducing the first reaction solution to the chip carrier with DNA nanoballs and standing same for 3 minutes to form the first layer of polymer film.

In one embodiment, after step 102, the preparation method further includes step 103. In step 103, the chip carrier reacted in step 102 is placed in a second reaction solution for reaction to form a second layer of polymer film on the first polymer film, the second reaction solution including a negatively charged polymer. The reaction time is 3 minutes. A concentration of polymers of the second reaction solution is 2 mg/mL. A dispersion liquid of the first reaction solution is a neutral buffer solution, such as PBS solution, TE buffer solution, or the like. The negatively charged polymer is dispersed in the dispersion liquid to form the second reaction solution.

The negatively charged polymer includes, but is not limited to, sodium hyaluronate, sodium polyacrylate, or sodium polystyrene sulfonate.

In one embodiment, step 103 includes introducing the second reaction solution on the chip carrier carrying the first layer of polymer film and standing for 3 minutes to form the second layer of polymer film. The first layer of polymer film and the second layer of polymer film together constitute the composite polymer film.

The reaction mechanism of the polymers, forming a polymer film wrapping the DNA nanoballs on the chip carrier, is as follows. The DNA nanoballs on the surface of the chip carrier are negatively charged under the condition of neutral pH or weakly acidic pH (above 5.5). When a positively charged polymer or a modified positively charged polymer is added, the positively charged polymer covers the DNA nanoballs through positive and negative interaction. The positively charged polymer already being added, when the negatively charged polymer is then added, the negatively charged polymer covers the positively charged polymer, through positive and negative interaction. That is, through a layer-by-layer self-assembly process, the composite polymer film is formed on the DNA nanoballs. When the zwitterionic polymer is added, the zwitterionic polymer is completely dissolved in a high-salt environment, and the positive charge on the zwitterionic polymer interacts with the DNA nanoballs, so that the zwitterionic polymer covers the surface of the DNA nanoballs. The high molecular weight of the polymer causes a network structure to be formed on the surface of the DNA nanoballs, and thereby the DNA nanoballs are stably in place on the surface of the chip carrier. When the polymer includes anti-protein components such as polyethylene glycol, derivatives of polyethylene, or betaine, the polymer film formed on the surface of the DNA nanoballs prevents nonspecific adsorption.

In one embodiment, between steps 101 and 102, the preparation method further includes introducing alcohol, such as isopropyl alcohol, to dewater the DNA nanoballs. The DNA nanoballs can then collapse better, to expose more negative charges on the surface.

In one embodiment, between steps 101 and 102 and after step 103, the preparation method further includes introducing a neutral buffer solution, such as PBS solution, on the chip carrier to remove excess polymers.

In one embodiment, after introducing neutral buffer solution on the chip carrier to remove recess polymers, the preparation method further includes introducing 5×SCC buffer solution including sequencing primers on the chip carrier to prepare the gene chip to be tested on the machine.

Example 1

The DNA nanoballs were added to a buffer solution to adjust the pH of the buffer solution to about 4.7, the mixture was introduced on the aminated silicon wafer, and after standing for 30 minutes, the alcohol was added to dewater the DNA nanoballs. Then 2 mg/mL of chitosan of medium molecular weight in 1% acetic acid solution was introduced, and NaOH was introduced to adjust the pH to about 5.5. After standing for 3 minutes, PBS solution was introduced to wash away excess chitosan molecules. Then PBS solution containing sodium hyaluronate at a concentration of 2 mg/mL was introduced, and after standing for 3 minutes, PBS solution was introduced to wash away excess sodium hyaluronate, so far, the fixing of DNA nanoballs on the silicon wafer was completed. Finally, 5×SCC buffer solution including sequencing primers was introduced, the gene chip to be tested on the machine was obtained.

The chitosan of medium molecular weight was purchased from Sigma Aldrich, the sodium hyaluronate (Mw 70,000~2-4 million Da) was purchased from Sango Biotech.

The general structural formula of the medium molecular weight chitosan is

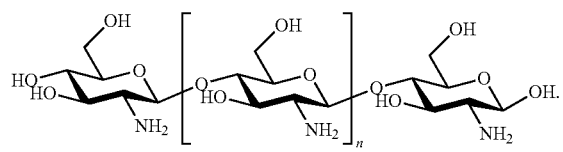

The general structural formula of the sodium hyaluronate is

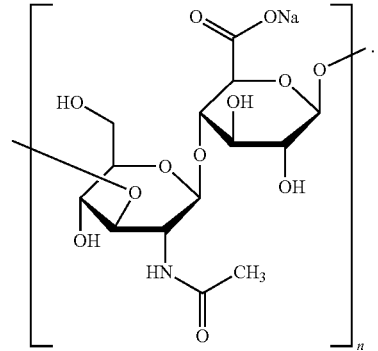

In example 1, the fixing mechanism of using polymer film to fix DNA nanoballs is as follows. First, the DNA nanoballs are assembled on the surface of the aminated silicon wafer, then the chitosan covers the surface of the DNA nanoballs through the interaction of its own positive charge and the negative charge on the surface of the DNA nanoballs. Then, the sodium hyaluronate covers the upper layer of the chitosan through the positive and negative interaction, so as to complete the fixing of every DNA nanoball on the surface of the chip. Because the chitosan and the sodium hyaluronate have strong water retention, the surface dryness of the obtained gene chip is reduced and delayed.

Example 2

The DNA nanoballs were added to a buffer solution to adjust the pH of the buffer solution to about 4.7, the mixture was introduced on the aminated silicon wafer, and after standing for 30 minutes, the alcohol was added to dewater the DNA nanoballs. Then 2 mg/mL of medium molecular weight chitosan in 1% acetic acid solution was introduced, and NaOH was introduced to adjust the pH to about 5.5. After standing for 3 minutes, PBS solution was introduced to wash away excess chitosan molecules, and thereby the fixing of DNA nanoballs on the silicon wafer was completed. Finally, neutral buffer solution was introduced, the gene chip to be tested on the machine was obtained. In example 2, the sodium hyaluronate in example 1 was removed, and only chitosan was used to prepare the gene chip. Compared with example 1, the water retentiveness of surface of the gene chip obtained in example 2 was slightly lower.

Example 3

10 mg/mL PLL (polylysine) aqueous solution was diluted with PBS solution to obtain 1 mg/mL PLL aqueous solution, then $CH_3$-PEG-NHS (PEG molecular weight is 2000) equivalent to half of the amino group in the polylysine backbone was added. After reacting for 30 minutes, PBS solution containing PLL-PEG was obtained. Then the DNA nanoballs were added to a buffer solution to adjust the pH of the buffer solution to about 4.7, the mixture was introduced on the aminated silicon wafer, and after standing for 30 minutes, the alcohol was added to dewater the DNA nanoballs. Then PBS solution containing PLL-PEG at a concentration of 2 mg/mL was introduced, and after standing for 3 minutes, PBS solution was introduced to wash away excess macromolecule (PLL-PEG). So far, the fixing of DNA nanoballs on the silicon wafer was completed. Finally, 5×SCC buffer solution including sequencing primers was introduced, the gene chip to be tested on the machine was obtained. The polylysine (Mw300,000) was purchased from Sango Biotech, and the $CH_3$-PEG-NHS (Mw2000) was purchased from Ponsure Biotechnology. Because PEG has strong anti-nonspecific adsorption characteristics, the surface nonspecific adsorption property of the gene chip is improved significantly.

Comparative Example

The DNA nanoballs were added to a buffer solution to adjust the pH of the buffer solution to about 4.7, the mixture was introduced on the aminated silicon wafer, and after standing for 30 minutes, the alcohol was added to dewater the DNA nanoballs. Then denatured bovine serum albumin was added to cover the surface of the DNA nanoballs, and then alcohol was added to remove the water from the bovine serum albumin layer. Finally, 5×SCC buffer solution including sequencing primers was introduced, thus the gene chip to be tested on the machine was obtained.

Fluorescent dNTP was added to the gene chips prepared in examples 1 to 3 and comparative examples to carry out DNA sequencing.

Figure 2A:
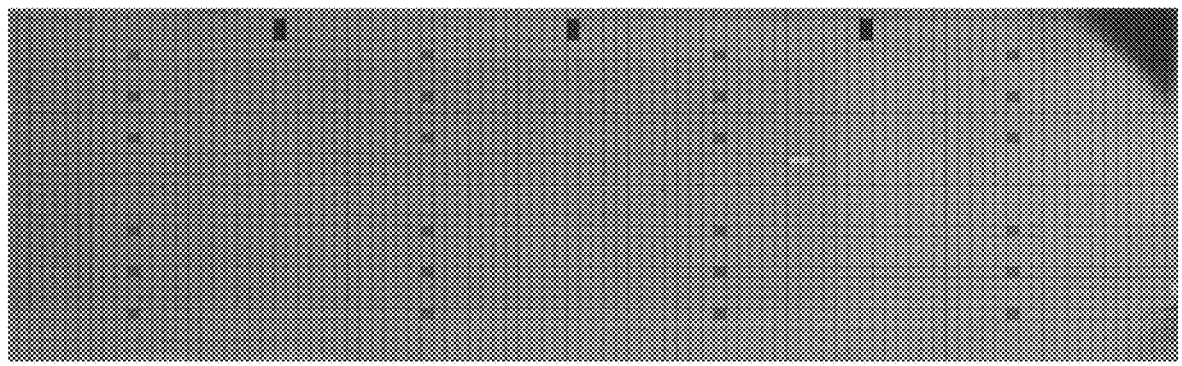
FIG. 2(a) shows a fluorescing photo of the gene chip prepared with chitosan-hyaluronic acid complex according to the example 1.
Figure 2B:
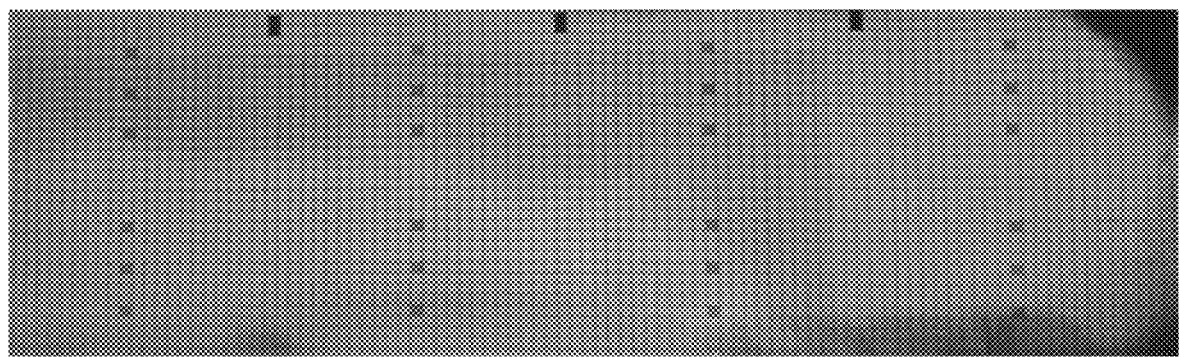
FIG. 2(b) shows a fluorescing photo of the gene chip prepared with chitosan according to the example 2.
Figure 2C:
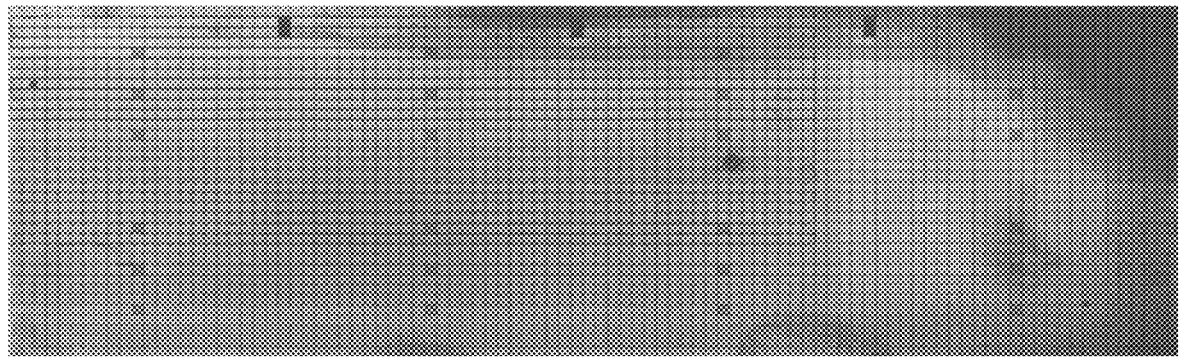
FIG. 2(c) shows the gene chip prepared by convention methods according to the comparative example.

FIGS. 2(a)-2(c) show fluorescing photos of the gene chips prepared in examples 1 and 2 and the comparative examples, used to reflect the dry condition of the surfaces of the gene chips. FIG. 2(a) shows the gene chip prepared with chitosan-hyaluronic acid complex which is prepared in example 1, FIG. 2(b) shows the gene chip prepared with chitosan which is prepared in the example 2, and FIG. 2(c) shows the gene chip prepared by conventional methods is prepared in the comparative example. The black area in the fluorescing photo of the gene chip prepared in the comparative example is formed due to the damage suffered by the DNA nanoballs caused by local drying. The damaged DNA nanoballs cannot be excited to fluoresce, which causes the sequencing of this area to fail, so that the black area appears. In the fluorescing photo of the gene chip prepared in example 1, there are only a few black areas, that is, the problem of surface dryness is significantly solved in the gene chip prepared in example 1. In the gene chip prepared in example 2, the problem of surface dryness is also improved, but the water retentiveness of gene chip of example 2 is slightly lower than that of example 1.

The Table 1 following is a comparison table of SE100 sequencing quality of gene chips prepared in examples 1 and 2 and the comparative example. The DNA nanoballs are fixed by the composite polymer film formed by the chitosan and sodium hyaluronate in example 1, the DNA nanoballs are fixed by the chitosan in example 2, and the DNA nanoballs are fixed by protein in comparative example. Compared with the comparative example, the fixing of the DNA nanoballs (reflected in Q30 and effective reading rate) in examples 1 and 2 is equivalent or better. In the sequencing of SE100 cycles, the DNA nanoballs can stably exist on the silicon wafers of the gene chips prepared in examples 1 and 2. Compared with the comparative example, the base reads in example 1 and example 2 are respectively increased by 13.38% and 7.51%.

TABLE 1

|  | example 1 (chitosan and sodium hyaluronate) | example 2 (chitosan) | comparative example (conventional methods) |
| --- | --- | --- | --- |
| Base reads (M) | 450.32 | 412.45 | 383.63 |
| Q30 (%) | 90.25 | 89.12 | 86.77 |
| effective reading rate (%) | 79.27 | 77.41 | 71.3 |

The Table 2 following is a comparison table of SE100+PE100 sequencing quality of gene chips prepared in examples 1 and 2 and comparative example. The DNA nanoballs are fixed by the composite polymer film formed by the chitosan and sodium hyaluronate in example 1, by the chitosan in example 2, and by protein in comparative example. Compared with the comparative example, the fixing of the DNA nanoballs (reflected in Q30 and effective reading rate) in examples 1 and 2 is equivalent or better. In the sequencing of SE100+PE100 cycles, the DNA nanoballs can stably exist on the silicon wafers of the gene chips prepared in examples 1 and 2. Compared with the comparative example, the base reads in example 1 and example 2 are respectively increased by 13.32% and 8.65%.

TABLE 2

|  | example 1 (chitosan and sodium hyaluronate) | example 2 (chitosan) | comparative example (conventional methods) |
| --- | --- | --- | --- |
| Base reads (M) | 736.42 | 706.09 | 649.86 |
| Q30 (%) | 87.12 | 86.30 | 86.15 |
| effective reading rate (%) | 78.73 | 75.54 | 69.82 |

Figure 3A:
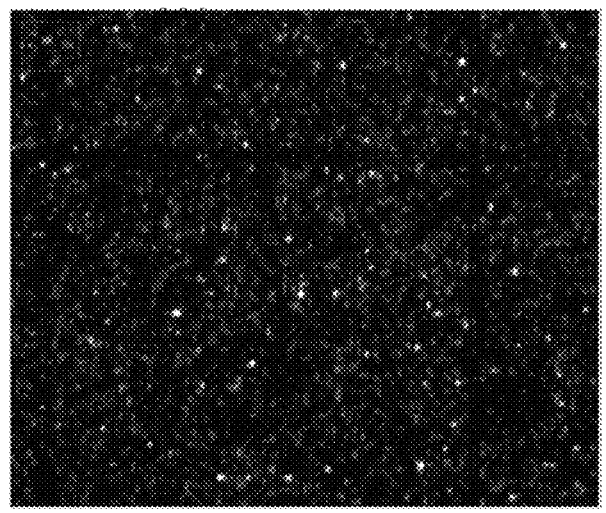
FIG. 3(a) shows a sequencing image of the comparative example.
Figure 3B:
FIG. 3(b) shows the sequencing image of the third example.

FIGS. 3(a) and 3(b) show sequencing images of the gene chips prepared in example 3 and comparative example, FIG. 3(a) shows the sequencing image of the comparative example, and FIG. 3(b) shows the sequencing image of example 3. Referring to FIGS. 3(a) and 3(b), the gene chip prepared in the comparative example has more bright spots on the surface of the gene chip due to protein aggregation caused by non-specific adsorption, while the gene chip prepared in example 3 has almost no bright spots on the surface. The lack of bright spots indicates that the use of modified positively charged polymer PLL-PEG to fix the DNA nanoballs in example 3 effectively reduces protein aggregation caused by surface nonspecific adsorption of the gene chip.

In the preparation method of the present disclosure, the reaction time for the polymer film to fix the DNA nanoballs can be completed within a short time (about 3 minutes), the production efficiency is high. The gene chip prepared by the preparation method of the present disclosure has good sequencing quality, and the problems of surface dryness and surface non-specific adsorption can be significantly reduced by selecting different polymer coatings.

Even though information and advantages of the present embodiments have been set forth in the foregoing description, together with details of the structures and functions of the present embodiments, the disclosure is illustrative only. Changes may be made in detail, especially in matters of shape, size, and arrangement of parts within the principles of the present exemplary embodiments, to the full extent indicated by the plain meaning of the terms in which the appended claims are expressed.

What is claimed is:

1. A gene chip comprising:
   a chip carrier;
   a plurality of DNA nanoballs assembled on the chip carrier; and
   a polymer film formed on the chip carrier and wrapping the plurality of DNA nanoballs;
   wherein the polymer film comprises at least one of a film of a positively charged polymer, a film of a positively charged polymer which is modified, a film of a zwitterionic polymer, and a composite polymer film, wherein the composite polymer film is formed by a layer-by-layer self-assembly process of the positively charged polymer and a negatively charged polymer.

2. The gene chip of claim 1, wherein the positively charged polymer comprises at least one of chitosan, polylysine, polyethyleneimine, poly-N,N-dimethylaminoethyl methacrylate, and a polymer with pyridyl side groups, imidazole salt side groups, and quaternary phosphate salt side groups.

3. The gene chip of claim 1, wherein the chip carrier is an aminated silicon wafer.

4. The gene chip of claim 1, wherein the zwitterionic polymer comprises at least one of polyacrylamide polymer and betaine polymer.

5. The gene chip of claim 1, wherein the negatively charged polymer comprises at least one of sodium hyaluronate, sodium polyacrylate, and sodium polystyrene sulfonate.

6. The gene chip of claim 1, wherein the positively charged polymer is modified by polyethylene glycol or polyethylene glycol derivatives.

7. A method of preparing a gene chip comprising:
   placing a chip carrier assembled with DNA nanoballs into a first reaction solution to form a first layer of polymer film covering the DNA nanoballs on the chip carrier, wherein the first reaction solution comprises at least one of a positively charged polymer, a positively charged polymer which is modified, and a zwitterionic polymer.

8. The preparation method of claim 7, further comprising placing the chip carrier, after reacting in the first reaction solution, into a second reaction solution to form a second layer of polymer film on the first layer of polymer film, wherein the second reaction solution comprises a negatively charged polymer.

9. The method of claim 8, further comprising introducing neutral buffer solution on the chip carrier to remove excess polymers.

10. The method of claim 8, wherein the positively charged polymer comprises at least one of chitosan, polylysine, polyethyleneimine, poly-N,N-dimethylaminoethyl methacrylate, and polymer with pyridyl side groups, imidazole salt side groups, and quaternary phosphate salt side groups.

11. The method of claim 8, wherein a concentration of polymers of the first reaction solution is 1 to 2 mg/mL, a reaction time in the first reaction solution is 3 minutes.

12. The method of claim 7, further comprising placing the chip carrier into a buffer solution containing the DNA nanoballs to assemble the DNA nanoballs on the surface of the chip carrier.

13. The method of claim 12, wherein after placing the chip carrier into a buffer solution containing the DNA nanoballs to react to assemble the DNA nanoballs on the surface of the chip carrier, the method further comprises introducing alcohol to dewater the DNA nanoballs.

14. The method of claim 8, wherein the zwitterionic polymer comprises at least one of polyacrylamide polymer and betaine polymer.

15. The method of claim 8, wherein the negatively charged polymer comprises at least one of sodium hyaluronate, sodium polyacrylate, and sodium polystyrene sulfonate.

16. The method of claim 8, wherein the positively charged polymer is modified by polyethylene glycol or polyethylene glycol derivatives.

17. The method of claim 8, wherein a concentration of polymers of the second reaction solution is 2 mg/mL, a reaction time in the second reaction solution is 3 minutes.

18. The method of claim 8, wherein a dispersion liquid of the first reaction solution is a neutral buffer solution or a weakly acidic buffer solution with a pH of 5.5 or more.

19. The method of claim 8, wherein a dispersion liquid of the second reaction solution is a neutral buffer solution.

* * * * *